United States Patent
Yoon et al.

(10) Patent No.: US 7,183,442 B2
(45) Date of Patent: Feb. 27, 2007

(54) PURIFICATION METHOD OF TEREPHTHAL ALDEHYDE

(75) Inventors: Hyun-kyung Yoon, Seoul (KR);
Won-ho Lee, Daejeon (KR);
Jong-hyun Chae, Daejeon (KR);
Dong-il Lee, Dongducheon-si (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/294,526

(22) Filed: Dec. 6, 2005

(65) Prior Publication Data

US 2006/0167320 A1    Jul. 27, 2006

(30) Foreign Application Priority Data

Jan. 26, 2005   (KR) .................... 10-2005-0007156

(51) Int. Cl.
*C07C 45/90*   (2006.01)

(52) U.S. Cl. ....................................... 568/438

(58) Field of Classification Search ............... None
See application file for complete search history.

(56) References Cited

U.S. PATENT DOCUMENTS

| | | | |
|---|---|---|---|
| 2,888,488 A | 5/1959 | Nace | |
| 4,017,547 A * | 4/1977 | Simmons et al. | 568/431 |
| 4,978,802 A * | 12/1990 | Campo et al. | 568/432 |

FOREIGN PATENT DOCUMENTS

JP        2001-199910        7/2001

* cited by examiner

*Primary Examiner*—Sikarl A. Witherspoon
(74) *Attorney, Agent, or Firm*—McKenna Long & Aldridge LLP

(57) ABSTRACT

The present invention relates to a method for preparing high-purity terephthalaldehyde from terephthalaldehyde crystal containing impurities by recrystallization using an antisolvent. Low-purity terephthalaldehyde prepared by a conventional method, which contains a small amount of impurities, is dissolved in a solvent and recrystallized using water as antisolvent to obtain high-purity terephthalaldehyde. The invention is significantly advantageous in using water only as antisolvent. Also, the purification process takes short time and is economical and environment-friendly.

5 Claims, No Drawings

PURIFICATION METHOD OF TEREPHTHAL ALDEHYDE

This application claims the benefit of the filing date of Korean Patent Application No. 10-2005-0007156, filed on Jan. 26, 2005 in the Korean Intellectual Property Office, the disclosure of which is incorporated herein in its entirety by reference.

TECHNICAL FIELD

The present invention relates to a purification method of terephthalaldehyde. Particularly, it relates to a purification method of terephthalaldehyde by adding an antisolvent to terephthalaldehyde dissolved in a solvent to precipitate high-purity terephthalaldehyde crystal. More particularly, the invention relates to a method for preparing high-purity terephthalaldehyde by recrystallization using water as antisolvent.

BACKGROUND ART

Aromatic aldehydes are useful in many applications since they have highly reactive aldehyde groups. Particularly, terephthalaldehyde having two aldehyde groups, see formula 1 below, is gaining focus as basic material of medicines, agrichemicals, pigments, liquid crystal polymers, conducting polymers, heat-resistant plastics, etc.

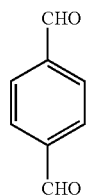

(1)

Terephthalaldehyde is a sublimable white solid having a molecular weight of 134.13 and a melting point of 114–116° C. It is known to be highly soluble in alcohols and be soluble in ether, alkali solutions and hot water.

Terephthalaldehyde, the material to be purified by the present invention, is prepared by known methods.

Hereunder is a brief description of the methods for preparing terephthalaldehyde.

Terephthalaldehyde can be prepared by dehydration of a chlorinated intermediate, hydrogenation of methyl terephthalate, oxidation of p-xylene in vapor phase, and so forth.

Terephthalaldehyde should be purified to high purity in order to be used in polymer synthesis or fine chemical process. For this purpose, such impurities as benzaldehyde, p-tolualdehyde and 4-hydroxybenzaldehyde should be removed.

Thus, the object of the present invention is to provide a method for purifying terephthalaldehyde obtained by conventional preparation methods to such a high purity as to be directly used in polymer synthesis or fine chemical process.

There are few reports of the purification methods of terephthalaldehyde for use in polymer synthesis or fine chemical process through effective removal of impurities.

U.S. Pat. No. 2,888,488 discloses a method for preparing terephthalaldehyde in which the product is purified by solvent extraction, drying and sublimation. However, this method entails a complicated process and uses chloroform, an environment-unfriendly compound, as solvent.

Japan Patent Laid-Open No. 2001-199910 discloses a method for recrystallizing aromatic aldehyde by cooling. But, this method is also limited in obtaining high-purity terephthalaldehyde.

DISCLOSURE OF INVENTION

It is an object of the present invention to solve the above-mentioned problems and to provide a method for obtaining high-purity terephthalaldehyde from low-purity. terephthalaldehyde by an economical and environment-friendly purification process. For this purpose, the present invention provides a method for obtaining high-purity terephthalaldehyde by dissolving terephthalaldehyde prepared by a conventional method and low-purity terephthalaldehyde with a small amount of impurities in a solvent and recrystallizing terephthalaldehyde using an antisolvent. Since water is used as antisolvent, this method is both economical and environment-friendly. It is also advantageous in that purification can be performed in short time.

To attain the object, the present invention provides a purification method of terephthalaldehyde.

The present invention relates to a method for obtaining high-purity terephthalaldehyde by dissolving terephthalaldehyde crystal containing impurities in a solvent and recrystallizing it using an antisolvent.

More particularly, the invention relates to a method for obtaining high-purity terephthalaldehyde by dissolving terephthalaldehyde in an alcohol and recrystallizing it using water as antisolvent.

Hereunder is given a more detailed description of the present invention.

The low-purity terephthalaldehyde to be purified by the present invention may be prepared by a conventional terephthalaldehyde preparation method or be purchased from the market.

For the solvent dissolving the terephthalaldehyde, alcohols, such as methanol, ethanol, propanol, isopropyl alcohol and diol, or acetone may be used. Preferably, methanol or ethanol is used.

Amount of the solvent is not particularly limited. Preferably, it is used in such an amount that is close to the solubility of the terephthalaldehyde crystal in the solvent.

Water, or the antisolvent, may be common purified water, including distilled water and deionized water. Use of water as antisolvent is desirable in terms of environment protection.

Amount of the solvent and the antisolvent may be adjusted depending on the yield of terephthalaldehyde, etc. Preferably, the mass proportion of the antisolvent to the solvent is 1:1 or larger. More preferably, it is from 1:1 to 10:1. If the mass proportion of the antisolvent to the solvent smaller than 1, yield may decrease. Otherwise, if it exceeds 10, amount of waste water may increase.

Purification of terephthalaldehyde according to the present invention is accomplished by dissolving terephthalaldehyde in a solvent, adding water, an antisolvent to the solvent, at a mass proportion of 1 to 10 and letting it alone for several minutes to several hours, so that the terephthalaldehyde is recrystallized. Of course, temperature during the recrystallization may be varied depending upon the solubility in the solvent.

Subsequently, the recrystallized terephthalaldehyde is filtered and dried. The drying may be performed by conventional methods, using a dry oven or a vacuum desiccator, at various temperature and time. Preferably, the drying is performed at 60–80° C. for 20–28 hours.

In case a higher purity is required, the above-mentioned recrystallization process may be performed for two or more times.

BEST MODE FOR CARRYING OUT THE INVENTION

Hereinafter, the present invention is described in further detail through examples. However, the following examples are only for the understanding of the invention and the invention is not limited to or by them.

EXAMPLES

Example 1

5 g of crude terephthalaldehyde was added to 40 g of methanol and completely dissolved while stirring well at room temperature. To the resultant solution was added 20 g of water, an antisolvent (mass proportion of water to methanol=0.5:1). After terephthalaldehyde was recrystallized, it was let alone at room temperature for 1 hour, filtered and dried at 70° C. for 24 hours to obtain recrystallized terephthalaldehyde.

Purity of terephthalaldehyde before and after purification was measured by gas chromatography-mass spectrometry (GC-MSD). Purity of terephthalaldehyde before purification was 97.2%. Terephthalaldehyde of the same purity was used in other examples, too. Purity of terephthalaldehyde after purification terephthalaldehyde is given in Table 1 below.

Example 2

Terephthalaldehyde purified in the same manner as in Example 1, except for adding 40 g of water as antisolvent (mass proportion of water to methanol=1:1). Purity of the obtained terephthalaldehyde was measured by GC-MSD.

Example 3

Terephthalaldehyde purified in the same manner as in Example 1, except for adding 120 g of water as antisolvent (mass proportion of water to methanol=3:1). Purity of the obtained terephthalaldehyde was measured by GC-MSD.

Example 4

Terephthalaldehyde purified in the same manner as in Example 1, except for adding 200 g of water as antisolvent (mass proportion of water to methanol=5:1). Purity of the obtained terephthalaldehyde was measured by GC-MSD.

Example 5

Terephthalaldehyde purified in the same manner as in Example 1, except for adding 280 g of water as antisolvent (mass proportion of water to methanol=7:1). Purity of the obtained terephthalaldehyde was measured by GC-MSD.

Example 6

Terephthalaldehyde purified in the same manner as in Example 1, except for adding 400 g of water as antisolvent (mass proportion of water to methanol=10:1). Purity of the obtained terephthalaldehyde was measured by GC-MSD.

Example 7

Terephthalaldehyde purified in the same manner as in Example 1, except for dissolving 5 g of crude terephthalaldehyde in 40 g ethanol at 55° C. and using 200 g of water as antisolvent (mass proportion of water to ethanol mass proportion=5:1). Purity of the obtained terephthalaldehyde was measured by GC-MSD.

Comparative Example 1

5 g of crude terephthalaldehyde was completely dissolved in 40 g of methanol at room temperature. After cooling at 0° C. for 1 hour and filtering, drying was performed at 70° C. for 24 hours to obtain recrystallized terephthalaldehyde. Purity of the terephthalaldehyde was measured by GC-MSD.

Comparative Example 2

5 g of crude terephthalaldehyde was completely dissolved in 30 g of methanol at 55° C. After cooling at 0° C. for 3 hours and filtering, drying was performed at 70° C. for 24 hours to obtain recrystallized terephthalaldehyde. Purity of the terephthalaldehyde was measured by GC-MSD.

TABLE 1

|  | Antisolvent | Solvent | Mass proportion (antisolvent to solvent) | Yield of TPAL (%) | Purity after purification (%) | Remarks |
| --- | --- | --- | --- | --- | --- | --- |
| Example 1 | Water | Methanol | 0.5:1 | 38.8 | 99.6 |  |
| Example 2 | Water | Methanol | 1:1 | 56.4 | 99.9 |  |
| Example 3 | Water | Methanol | 3:1 | 71.8 | 99.7 |  |
| Example 4 | Water | Methanol | 5:1 | 78.6 | 99.7 |  |
| Example 5 | Water | Methanol | 7:1 | 79 | 99.6 |  |
| Example 6 | Water | Methanol | 10:1 | 79.2 | 99.6 |  |
| Example 7 | Water | Ethanol | 5:1 | 76.8 | 99.9 |  |
| Comp. Example 1 | — | Methanol | — | 0.2 | — | Cooling method |
| Comp. Example 2 | — | Methanol | — | 48 | 99.3 | Cooling method |

As seen in Table 1, when purification was made using water as antisolvent according to the present invention (Examples 1–7), terephthalaldehyde could be obtained in higher purity as compared with those obtained by cooling method (Comparative Examples 1 and 2).

INDUSTRIAL APPLICABILITY

In accordance with the present invention, high-purity terephthalaldehyde can be obtained by dissolving terephthalaldehyde in a solvent and using water as antisolvent. Since water is used as antisolvent, the purification process is simple and environment-friendly. Also, there is an advantage of preparing high-purity terephthalaldehyde at low cost.

While the present invention has been described in detail with reference to the preferred embodiments, those skilled in the art will appreciate that various modifications and substitutions can be made thereto without departing from the spirit and scope of the invention as set forth in the appended claims.

The invention claimed is:

1. A purification method of terephthalaldehyde comprising the steps of dissolving terephthalaldehyde crystal containing impurities in a solvent and recrystallizing same using an antisolvent.

2. The purification method of claim 1, said solvent being at least one selected from a group consisting of methanol, ethanol, propanol, isopropyl alcohol, diol and acetone.

3. The purification method of claim 1, said antisolvent being water.

4. The purification method of claim 1, mass proportion of said antisolvent to said solvent being at least 1.

5. The purification method of claim 1, mass proportion of said antisolvent to said solvent being 1–10.

* * * * *